United States Patent
Tolle et al.

(10) Patent No.: US 7,727,953 B2
(45) Date of Patent: Jun. 1, 2010

(54) CRYSTALLINE FORM OF A DRUG

(75) Inventors: John C. Tolle, Kansasville, WI (US); Ahmad Y. Sheikh, Deerfield, IL (US)

(73) Assignee: Abbott Laboratories Inc., Abbott Park, IL (US)

( * ) Notice: Subject to any disclaimer, the term of this patent is extended or adjusted under 35 U.S.C. 154(b) by 257 days.

(21) Appl. No.: 11/615,234

(22) Filed: Dec. 22, 2006

(65) Prior Publication Data

US 2007/0185034 A1     Aug. 9, 2007

Related U.S. Application Data

(60) Provisional application No. 60/754,743, filed on Dec. 29, 2005.

(51) Int. Cl.
*A01N 37/18*    (2006.01)
*A61K 38/00*    (2006.01)
*G01N 31/00*    (2006.01)

(52) U.S. Cl. .............................................. 514/2; 436/4

(58) Field of Classification Search ........................ None
See application file for complete search history.

(56) References Cited

U.S. PATENT DOCUMENTS

| 6,716,963 | B1 | 4/2004 | Henkin |
| 6,774,211 | B1 | 8/2004 | Henkin |
| 2002/0830650 |  | 4/2002 | Henkin |

OTHER PUBLICATIONS

Polymorphism in Pharmaceutical Solids, edited by Brittain, 1999, Macel Dekker Inc., pp. 178-179, 185 and 219.*
Concise Encyclopedia of Chemistry (1993), Walter de Gruyter, Berlin-New York.*
Haleblian et al. Journal of Pharmaceutical Sience, Aug. 1969, vol. 58, No. 8, pp. 911-929.*
Rouhi, A.M., Chemical & Engineering New, Feb. 24, 2004, pp. 32-35.*

* cited by examiner

*Primary Examiner*—Suzanne M. Noakes
(74) *Attorney, Agent, or Firm*—Glen J. Gesicki

(57) ABSTRACT

Ac-Sar-Gly-Val-D-allo-Ile-Thr-Nva-Ile-Arg-ProNHCH$_2$CH$_3$ Crystalline Form 1, ways to make it, compositions containing it and methods of treatment of diseases and inhibition of adverse physiological events using it are disclosed.

3 Claims, 1 Drawing Sheet

CRYSTALLINE FORM OF A DRUG

This application claims priority to U.S. Provisional Parent Application Ser. No. 60/754,743, filed Dec. 29, 2005.

FIELD OF THE INVENTION

This invention pertains to a crystalline form of Ac-Sar-Gly-Val-D-allo-Ile-Thr-Nva-Ile-Arg- ProNHCH$_2$CH$_3$, ways to make it, compositions containing it and methods of treatment of diseases and inhibition of adverse physiological events using it.

BACKGROUND OF THE INVENTION

The acetic acid salt of Ac-Sar-Gly-Val-D-allo-Ile-Thr-Nva-Ile-Arg-ProNHCH$_2$CH$_3$.CH$_3$CO$_2$H (AcXGVI*TNIRP NHCH$_2$CH$_3$.CH$_3$CO$_2$H) is useful for treating diseases that are caused or exacerbated by angiogenesis.

Because the crystallinity of this compound may effect, among other physical and mechanical properties, its solubility, dissolution rate, hardness, compressability and melting point, there is an existing need in the process and therapeutic arts for identification of crystalline forms of AcXGVI*TNIRPNHEt.CH$_3$CO$_2$H and ways of reproducibly making it.

SUMMARY OF THE INVENTION

Figure 1:
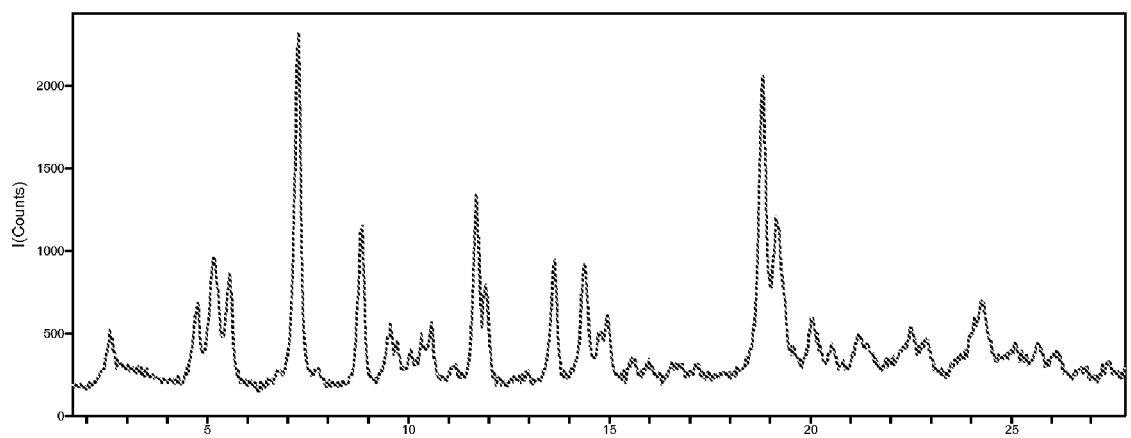
FIG. 1 shows a powder diffraction pattern of AcXGVI*TNIRPNHCH$_2$CH$_3$.CH$_3$CO$_2$H Crystalline Form 1.

One embodiment of this invention, therefore, pertains to AcXGVI*TNIRPNHCH$_2$CH$_3$.CH$_3$CO$_2$H Crystalline Form 1 characterized, when measured at about 25° C. with Cu-Kα radiation, by a powder diffraction pattern with at least three peaks having respective 2θ values of about 2.6, 4.7, 5.2, 5.5, 7.2, 8.9, 11.6, 13.6 or 14.4.

Another embodiment pertains to AcXGVI*TNIRPNHCH$_2$CH$_3$.CH$_3$CO$_2$H Crystalline Form 1 having substantial crystalline purity and characterized, when measured at about 25° C. with Cu-Kα radiation, by a powder diffraction pattern with at least three peaks having respective 2θ values of about 2.6, 4.7, 5.2, 5.5, 7.2, 8.9, 11.6, 13.6 or 14.4.

Still another embodiment pertains to AcXGVI*TNIRPNHCH$_2$CH$_3$.CH$_3$CO$_2$H Crystalline Form 1 having substantial crystalline purity and substantial chemical purity and characterized, when measured at about 25° C. with Cu-Kα radiation, by a powder diffraction pattern with at least three peaks having respective 2θ values of about 2.6, 4.7, 5.2, 5.5, 7.2, 8.9, 11.6, 13.6 or 14.4.

Still another embodiment pertains to compositions comprising an excipient and AcXGVI*TNIRPNHCH$_2$CH$_3$.CH$_3$CO$_2$H Crystalline Form 1.

Still another embodiment pertains to methods of treating diseases that are caused or exacerbated by angiogenesis in a mammal comprising administering thereto a therapeutically effective amount of a composition comprising or made from AcXGVI*TNIRPNHCH$_2$CH$_3$.CH$_3$CO$_2$H Crystalline Form 1.

DETAILED DESCRIPTION OF THE INVENTION

This invention pertains to discovery of AcXGVI*TNIRPNHCH$_2$CH$_3$.CH$_3$CO$_2$H Crystalline Form 1, ways to characterize it, compositions containing it and methods of treating diseases caused or exascerbated by angiogenesis using it.

The term "Ac," as used herein, means acetyl.

The term "Sar," or the symbol "X," as used herein, means sarcosyl.

The term "Gly," or the symbol "G," as used herein, means glyclyl.

The term "Val," or the symbol "V," as used herein, means valyl.

The term "D-allo-Ile," or the symbol "I*," as used herein, means D-allo-isolucinyl.

The term "Thr," or the symbol "T," as used herein, means threoninyl.

The term "Nva," or the symbol "N," as used herein, means norvalyl.

The term "Ile," or the symbol "I," as used herein, means isolucinyl.

The term "Arg," or the symbol "R," as used herein, means arginyl.

The term "Pro," or the symbol "P," as used herein, means prolinyl.

The term "diseases caused or exascerbated by angiogenesis," as used herein, means angiogenic diseases (e.g. diabetic retinopathy, retinopathy of prematurity, choroidal neovascularization due to age-related macular degeneration, infantile hemangiomas, cancer (lung, breast, stomach, bladder, colon, pancreatic, ovarian, prostate and rectal cancer and hematopoietic malignancies (leukemia and lymphoma), glioblastoma, infantile hemangioma)) (Lab. Investig. (1992), 67(4), 519-528; Anat. Rec. (1997), 249(1), 63-73; Int. J.Cancer (1995), 63(5), 694-701; Vasc. Biol. (1995), 15(11), 1857-6)), pulmonary hypertension in patients with thromboembolic disease (J. Thorac. Cardiovasc. Surg. 2001, 122 (1), 65-73), and autoimmune diseases (psoriasis, kidney rejection, graft versus host disease).

The term "amorphous," as used herein, means a super-cooled liquid substance or a viscous liquid which may appear as a solid but is not crystalline. Amorphous substances do not have a melting point but soften or flow above a certain temperature known as the glass transition temperature.

The term "crystalline," as used herein, means having a regularly repeating arrangement of molecules which is maintained over a long range or external face planes.

Unless stated otherwise, percentages herein are weight/weight (w/w) percentages.

The term "substantial crystalline purity," as used herein, means at least about 95% crystalline purity, preferably about 97% crystalline purity, more preferably about 99% crystalline purity, and most preferably about 100% crystalline purity.

The term "crystalline purity," as used herein, means percentage of a particular crystalline form of a compound in a sample which may contain amorphous form of the compound, one or more than one other crystalline forms of the compound other than the crystalline form of the compound of this invention, or a mixture thereof.

The term "substantial chemical purity," as used herein, means about 95% chemical purity, preferably about 97% chemical purity, more preferably about 98% chemical purity, and most preferably about 100% chemical purity.

The term "chemical purity," as used herein, means percentage of a particular compound in a sample.

The term "seed crystal," as used herein, means a particular crystalline form of a substance having mass. It is meant to be understood that such a crystal may be small enough to be airborne or invisible to the eye without means of detection.

A therapeutically acceptable amount of AcXG VI*TNIRPNHCH$_2$CH$_3$.CH$_3$CO$_2$H Crystalline Form 1 depends on recipient of treatment, disorder being treated and severity thereof, composition containing it, time of administration, route of administration, duration of treatment, its potency, its rate of clearance and whether or not another drug is co-administered. The amount of AcXGVI*TNIR PNHCH$_2$CH$_3$.CH$_3$CO$_2$H Crystalline Form 1 used to make a composition to be administered daily to a patient in a single dose or in divided doses is from about 0.03 to about 200 mg/kg body weight. Single dose compositions contain these amounts or a combination of submultiples thereof.

AcXGVI*TNIRPNHCH$_2$CH$_3$.CH$_3$CO$_2$H Crystalline Form 1 may be administered with or without an excipient. Excipients include but are not limited to, for example, encapsulating materials and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising and made with AcXGVI*TNIRPNHCH$_2$CH$_3$.CH$_3$CO$_2$H Crystalline Form 1 to be administered orally in solid dosage form include, for example, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl cellulose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising and made with AcXGVI*TNIRPNHCH$_2$CH$_3$.CH$_3$CO$_2$H Crystalline Form 1 to be administered ophthalmically or orally in liquid dosage forms include, for example, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising and made with AcXGVI*TNIRPNHCH$_2$CH$_3$.CH$_3$CO$_2$H Crystalline Form 1 to be administered osmotically include, for example, chlorofluorohydrocarbons, ethanol, water, mixtures thereof and the like. Excipients for preparation of compositions comprising and made with AcXGVI*TNIRPNHCH$_2$CH$_3$.CH$_3$CO$_2$H Crystalline Form 1 to be administered parenterally include, for example, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising and made with AcXGVI*TNIRPNHCH$_2$CH$_3$.CH$_3$CO$_2$H Crystalline Form 1 to be administered rectally or vaginally include, but are not limited to, cocoa butter, polyethylene glycol, wax, mixtures thereof and the like.

The following examples are presented to provide what is believed to be the most useful and readily understood description of procedures and conceptual aspects of this invention.

EXAMPLE 1

Ac-Sar-Gly-Val-D-allo-Ile-Thr-OH (2.14 Kg, 3.56 mol), Ile-Arg-ProNHEt dihydrochloride salt (1.00-1.06 equivalents) and 1-hydroxybenzotriazole (1.3 equivalents) were dissolved in dimethylformamide (14 Kg/Kg Ac-Sar-Gly-Val-D-allo-Ile-Thr-OH) at 28° C. The solution was cooled to −10° C. and treated with 2,4,6-collidine (2.1 mole equivalents) and 1-(3-dimethylaminopropyl)-3-ethylcarbodiimide (EDAC. HCl, 1.1-1.2 equivalents) in distilled water (1 Kg/Kg EDAC.HCl) while maintaining the temperature at −5° C. The mixture was monitored for the consumption of Ac-Sar-Gly-Val-D-allo-Ile-Thr-OH by HPLC, warmed to 20° C., treated with water (50 Kg/Kg of Ac-Sar-Gly-Val-D-allo-Ile-Thr-OH) while maintaining a temperature of 35° C., mstirred for 1 hour, adjusted to 20° C., adjusted to pH 5.4±0.6 with 1N sodium hydroxide or acetic acid, as needed and further diluted with water to provide a solution that contains about 5 g of EXAMPLE 1/Kg. This solution was suitable for reverse osmosis.

EXAMPLE 2

The solution of EXAMPLE 1 (3.44 Kg) was purified with a Nanomax 50 membrane cartridge in a NIRO reverse osmosis unit at 175±50 psi and a 20-30° C. The solution was diafiltered with distilled water (850 Kg/Kg) and concentrated 4× to provide a solution with about 20 g EXAMPLE 1/Kg of solution. This solution was diafiltered with 1% sodium acetate (pH 5.2±0.5, 930 Kg/Kg of EXAMPLE 1). The permeate solution was monitored for chloride by ion selective electrode until the salt exchange (chloride to acetate) was complete. The retentate was monitored for the removal of HOBt by HPLC until the process was complete. The product solution was diafiltered with 20 ppm acetic acid solution (870 Kg/Kg of EXAMPLE 1). The permeate solution was monitored by conductance for sodium acetate until the sodium acetate removal was complete. The retentate was monitored by HPLC for the removal of EDU until complete. The product solution was concentrated to about 80 g EXAMPLE 1/Kg of solution, drained to a container and washed twice with distilled water (4-5 Kg/Kg EXAMPLE 1). The rinses are combined with the product solution. The yield of AcXGVI*TNIRPNHCH$_2$CH$_3$ was about 90-97%.

EXAMPLE 3

The product solution of EXAMPLE 2 (1 Kg, about 42 g AcXGVI*TNIRPNHCH$_2$CH$_3$/Kg solution) was double filtered (0.45 and 0.2 μm filters in series) into a reactor. A distilled water (0.5 Kg) rinse of the filters, acetic acid (0.04 Kg, 0.6-0.7 mole equivalents) and isopropanol (25 Kg/Kg AcXGVI*TNIRPNHCH$_2$CH$_3$.CH$_3$CO$_2$H) are then added to the solution. The solution was distilled under vacuum at 50° C. to approximately 15 L. Additional isoproanol (30 Kg/Kg AcXGVI*TNIRPNHCH$_2$CH$_3$ and 14 Kg/Kg AcXGVI*TNIRPNHCH$_2$CH$_3$) was added, and the distillation was repeated twice. The concentration of water was monitored by Karl Fischer until a ratio of AcXGVI*TNIRPNHCH$_2$CH$_3$ (Kg)/water(L)/isopropanol(L) of 1:4:10 was obtained. The solution was warmed to 40° C., treated with isopropanol (4 Kg/Kg AcXGVI*TNIRPNHCH$_2$CH$_3$) to provide a ratio of AcXGVI*TNIRPNHCH$_2$CH$_3$(Kg)/water(L)/isopropanol(L)

of 1:4:15. Filtered isopropyl acetate (16 Kg/Kg AcXGVI*TNIRPNHCH$_2$CH$_3$) was added, and the mixture was cooled to 25° C. Additional filtered isopropyl acetate (39 Kg/Kg AcXGVI*TNIRPNHCH$_2$CH$_3$) was added at a rate of 6-9 Kg/h), and the mixture was stirred for 3 hours and filtered. The filtrate was washed with a mixture of isopropanol (3 Kg/Kg AcXGVI*TNIRPNHCH$_2$CH$_3$) and isopropyl acetate (14 Kg/Kg AcXGVI*TNIRPNHCH$_2$CH$_3$). The solids were dried under vacuum at 45° C. for 12 hours, de-lumped with a mortar and pestle and screened through Nos. 10 and 18 sieves. The solids may be hydrated by transferral to a dryer containing a pan of water. The dryer was held at 40° C. for 8-24 hours under vacuum and further dried under vacuum at 45° C. regardless of the optional moisture treatment. The drying was monitored by GC for the removal of isopropanol and isopropyl acetate until complete. The yield of AcXGVI*TNIRPNHCH$_2$CH$_3$.CH$_3$CO$_2$H was 86-94%.

A sample of AcXGVI*TNIRPNHCH$_2$CH$_3$.CH$_3$CO$_2$H Crystalline Form 1 for powder diffraction analysis was applied as a thin layer, with no prior grinding, to the analysis well of a Scintag×2 Diffraction Pattern System having the following parameters: x-ray source: Cu-K$\alpha$; range: 2.00°-40.00° 2$\theta$; scan rate: 1.00 degree per minute; step size: 0.02°; temperature: about 25° C.; wavelength: 1.54178 Å (Cu-K$\alpha$).

It is meant to be understood that peak heights may vary and will be dependent on variables such as the temperature, size of crystal size or morphology, sample preparation, or sample height in the analysis well of the Scintag×2 Diffraction Pattern System.

It is also meant to be understood that peak positions may vary when measured with different radiation sources. For example, Cu-K$\alpha_1$, Mo-K$\alpha$, Co-K$\alpha$ and Fe-K$\alpha$ radiation, having wavelengths of 1.54060 Å, 0.7107 Å, 1.7902 Å and 1.9373 Å, respectively, may provide peak positions that differ from those measured with Cu-K$\alpha$ radiation.

The term “about” preceding a series of peak positions is meant to include all of the peak positions of the group which it precedes.

The term “about” preceding a series of peak positions means that all of the peaks of the group which it precedes are reported in terms of angular positions with a variability of ±0.1°.

For example, the phrase about 2.6, 4.7, 5.2, 5.5, 7.2, 8.9, 11.6, 13.6 or 14.4 means about 2.6, about 4.7, about 5.2, about 5.5, about 7.2, about 8.9, about 11.6, about 13.6 or about 14.4 or 2.6±0.1°, 4.7±0.1°, 5.2±0.1°, 5.5±0.1°, 7.2±0.1°, 8.9±0.1°, 11.6±0.1°, 13.6±0.1°or 14.4±0.1°.

The foregoing is meant to be illustrative of the invention and not intended to limit it to the disclosed embodiments. Variations and changes obvious to one skilled in the art are intended to be within the scope and nature of the invention as defined in the claims.

We claim:

1. AcXGVI*TNIRPNHCH$_2$CH$_3$.CH$_3$CO$_2$H Crystalline Form 1 characterized, when measured at about 25° C. with Cu—K$\alpha$ radiation, by a powder diffraction pattern with peaks having respective 2$\theta$ values of about 2.6, 4.7, 5.2, 5.5, 7.2, 8.9, 11.6, 13.6, and 14.4.

2. AcXGVI*TNIRPNHCH$_2$CH$_3$.CH$_3$CO$_2$H Crystalline Form 1 having substantial crystalline purity and characterized, when measured at about 25° C. with Cu—K$\alpha$ radiation, by a powder diffraction pattern with peaks having respective 2$\theta$ values of about 2.6, 4.7, 5.2, 5.5, 7.2, 8.9, 11.6, 13.6, and 14.4.

3. AcXGVI*TNIRPNHCH$_2$CH$_3$.CH$_3$CO$_2$H Crystalline Form 1 having substantial crystalline purity and substantial chemical purity and characterized, when measured at about 25° C. with Cu—K$\alpha$ radiation, by a powder diffraction pattern with peaks having respective 2$\theta$ values of about 2.6, 4.7, 5.2, 5.5, 7.2, 8.9, 11.6, 13.6, and 14.4.

* * * * *